US010206664B2

(12) United States Patent
McGhie (10) Patent No.: US 10,206,664 B2
(45) Date of Patent: Feb. 19, 2019

(54) SPIRAL CUT BIOPSY CANNULA (71) Applicant: Cook Medical Technologies LLC, Bloomington, IN (US)

(72) Inventor: Thomas W. McGhie, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 14/538,991

(22) Filed: Nov. 12, 2014

(65) Prior Publication Data

US 2015/0133815 A1 May 14, 2015

Related U.S. Application Data (60) Provisional application No. 61/903,660, filed on Nov. 13, 2013.

(51) Int. Cl.
A61B 5/00 (2006.01)
A61B 10/02 (2006.01)
A61M 25/00 (2006.01)

(52) U.S. Cl.
CPC ..... *A61B 10/0275* (2013.01); *A61M 25/0054* (2013.01)

(58) Field of Classification Search
CPC .......... A61M 25/0054; A61M 25/0136; A61M 25/0138; A61M 25/065; A61B 10/0275
USPC ................................. 600/562–568
See application file for complete search history.

(56) References Cited

U.S. PATENT DOCUMENTS

| 5,441,483 | A | | 8/1995 | Avitall |
| 5,595,185 | A | | 1/1997 | Erlich |
| 5,741,429 | A | | 4/1998 | Donadio, III et al. |
| 5,779,647 | A | | 7/1998 | Chau et al. |
| 5,910,121 | A | | 6/1999 | Paolo et al. |
| 6,086,543 | A | * | 7/2000 | Anderson .......... A61B 10/0233 600/567 |
| 6,419,641 | B1 | * | 7/2002 | Mark .................. A61B 10/0275 600/564 |
| 6,428,489 | B1 | | 8/2002 | Jacobsen et al. |
| 7,063,672 | B2 | | 6/2006 | Schramm |
| 7,704,234 | B2 | * | 4/2010 | Darr .................... A61B 10/0275 604/164.01 |
| 8,206,409 | B2 | | 6/2012 | Privitera et al. |

(Continued)

FOREIGN PATENT DOCUMENTS

WO WO 97/24070 7/1997
WO WO 02/065919 8/2002

*Primary Examiner* — Max Hindenburg
(74) *Attorney, Agent, or Firm* — Woodard, Emhardt, Henry, Reeves & Wagner, LLP (57) ABSTRACT Disclosed is an instrument useful for taking tissue samples from human or animal patients that includes a cannula or other similar elongate body cooperating with a stylet or similar device coaxially positioned within the cannula such that the cannula and stylet are useful for capturing and excising tissue. The cannula body includes at least one flexing region having one or more slits disposed in a generally helical slit pattern arranged around and along the cannula. Methods for taking tissue samples from a patient are also disclosed including navigating the cannula and stylet through various internal structures of the patient's body where the flexing region aids to avoid binding between the cannula and the stylet during the procedure.

27 Claims, 7 Drawing Sheets

(56) References Cited

U.S. PATENT DOCUMENTS

| | | |
|---|---|---|
| 8,251,963 B2 | 8/2012 | Chin et al. |
| 9,044,216 B2 * | 6/2015 | O'Laughlin |
| 9,125,638 B2 * | 9/2015 | Chin ................. A61B 10/0275 |
| 2004/0133124 A1 | 7/2004 | Bates et al. |
| 2005/0015072 A1 | 1/2005 | Engel et al. |
| 2006/0264904 A1 | 11/2006 | Kerby et al. |
| 2009/0054807 A1 * | 2/2009 | Taylor ................ A61B 10/0275 600/567 |
| 2009/0143698 A1 | 6/2009 | Janssens |
| 2011/0160680 A1 * | 6/2011 | Cage ............... A61M 25/09033 604/265 |
| 2012/0065543 A1 | 3/2012 | Ireland |
| 2012/0245487 A1 | 9/2012 | Eells et al. |
| 2012/0289911 A1 | 11/2012 | Chin et al. |

* cited by examiner

SPIRAL CUT BIOPSY CANNULA

BACKGROUND

The present disclosure relates generally to medical devices and methods, and in particular aspects the disclosure is related to obtaining a tissue sample from an internal organ of a patient using a biopsy cannula or similar device.

Biopsy devices, such as a biopsy needle or biopsy cannula can be useful for collecting tissue from patients for the examination of the tissue for various manifestations of disease such as in the field of histopathology. These devices often use a coaxial stylet and cannula, or two cannulae, or other such devices to capture and excise the tissue from the patient, such as from an internal organ. The cannulae and stylets are typically steel and often do not work well when operated through a curve where an indirect approach through the patient's internal organs such as the vasculature structure is advantageous. Such a situation may arise, for example, when transluminal access is deemed the best approach, or an overlying organ prevents direct access, to name a few.

SUMMARY

Disclosed are various embodiments of a biopsy instrument for taking a tissue sample from human or animal patients. The various embodiments include instruments having a cannula with at least one tissue collector such as a stylet coaxially positioned within the cannula. Also disclosed is a pattern of slits passing at least part way through the cannula wall, the slits being part of a flexing region which increases the flexibility of the cannula, at least in the area of the flexing region. Various arrangements for the slits are disclosed, such as a generally helical slit pattern having slits disposed along one or more turns disposed both circumferentially around and longitudinally along the cannula. The cannula may also include a cutting surface disposed at or near the distal tip of the cannula that is useful for aiding in the process of excising a tissue sample.

The stylet may also include a penetrating member at its distal end, and a tissue receiving opening or tissue collection notch near the distal end as well. Various embodiments of an actuating assembly are also discussed for actuating the biopsy instrument to excise a tissue sample, and at least one example is disclosed of a method for using the biopsy instrument when taking the tissue sample and extracting it from the patient for further study.

Further forms, objects, features, aspects, benefits, advantages, and embodiments of the present invention will become apparent from the detailed description, drawings, and claims, provided herewith.

DETAILED DESCRIPTION

For the purpose of promoting an understanding of the principles of the invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the invention as described herein are contemplated as would normally occur to one skilled in the art to which the invention relates. One embodiment of the invention is shown in great detail, although it will be apparent to those skilled in the relevant art that some features not relevant to the present invention may not be shown for the sake of clarity.

Figure 1:
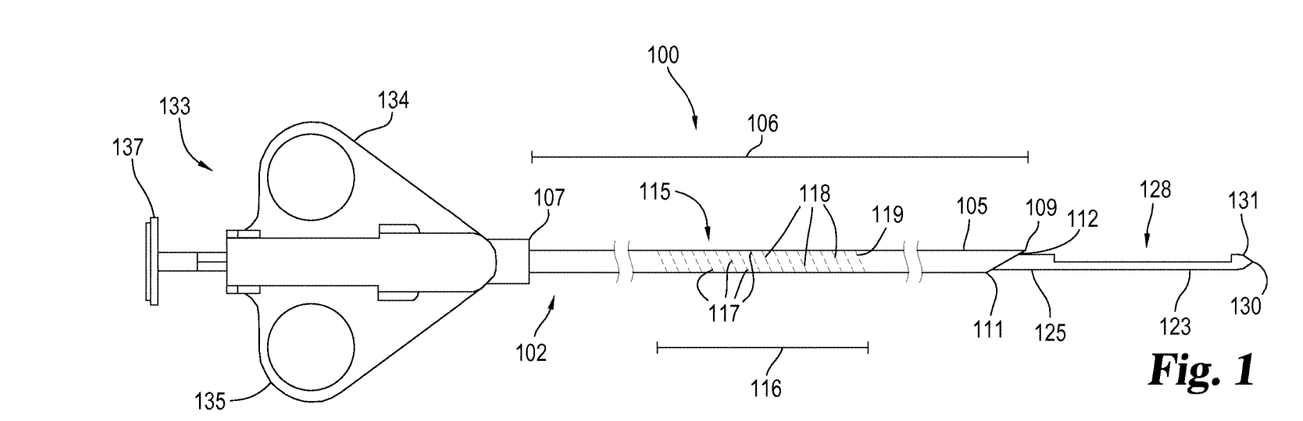
FIG. 1 is a diagrammatic view of a biopsy instrument of the present disclosure illustrating.
Figure 2:
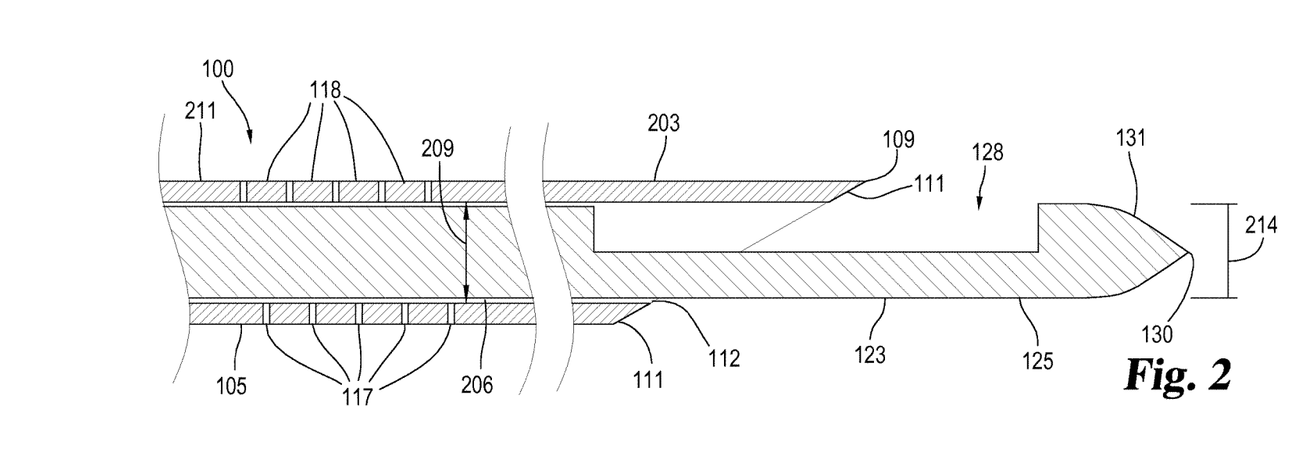
FIG. 2 is a partial cross-sectional view of the biopsy instrument of FIG. 1.

Illustrated in FIGS. 1 and 2 is one embodiment of a biopsy instrument 100 useful for collecting a tissue sample from a patient. Further detail is shown in FIGS. 3 through 6, while FIGS. 7A and 7B illustrate one example of how such an instrument might be used to collect a sample. Biopsy instrument 100 includes a first elongate body such as a cannula 102 within which a second elongate body such as a stylet 123 is coaxially disposed and received. In this configuration stylet 123 can operate as a tissue collector. For example, stylet 123 may be inserted into tissue to be sampled and then cannula 102 may be actuated to move over stylet 123 to excise or otherwise free the tissue sample so that it may be withdrawn with biopsy instrument 100. This type of procedure, and possibly other procedures as well, may be performed in areas of the patient that require cannula 102 and stylet 123 to twist, bend, or be otherwise deformed so as to navigate through the patient's anatomy, for example, through the patients vasculature. By navigating to the tissue sampling region internally, it may be possible to avoid disturbing other vital organs which may surround the sampling region. However, such a positioning of biopsy instrument 100 might cause cannula 102 to kink and possibly bind on stylet 123 when attempting to collect the tissue sample. To enhance the likelihood of success in positioning biopsy instrument 100 and taking a tissue sample, biopsy instrument 100 includes one or more flexing regions 115 which include one or more discontinuities or slits 117 separated by wall portions 118. The slits 117 and wall portions 118 may be arranged in a generally helical slit pattern 119 which can be advantageous for relieving stress from bending cannula 102 around corners within the patient while also advantageously allowing stylet 123 to move within cannula 102 without binding to retrieve the tissue sample.

Considering FIGS. 1 and 2 in further detail, the illustrated embodiment of elongate cannula body 105 has a length 106 measured from about a proximal end 107 to about a distal end 109 and has a generally tubular construction defining a cannula lumen 206 shown in the partial cut-away view in FIG. 2. Cannula lumen 206 has a lumen width 209 large enough to provide adequate clearance for a tissue collector or stylet 123 having an elongate collector body 125 with a collector body width 214. In the illustrated embodiment, elongate cannula body 105 also includes a cutting surface 111 at distal end 109 useful for separating the tissue sample from the patient as cannula body 105 is actuated to slide distally relative to stylet 123.

Cannula body 105 may be constructed using a variety of materials and structures. Cannula body 105 may have a single or multi-layer tubular construction, or use a combination thereof. For example, cannula body 105 may define cannula lumen 206 by a single tubular member formed by a single layer of material, or in another embodiment, by a tubular member having one or more layers of material that may be the same or different materials. Other embodiments of cannula body 105 may include more than one lumen as well, and may also include a lumen, or lumens, having other cross-sectional shapes such as ovals, hexagons, octagons, and various other polygonal shapes. In another embodiment, parts of cannula body 105 may be constructed of one or more materials, while other parts may be constructed of the same or different materials. For example, the materials used may vary from the proximal to the distal end. Some examples of suitable materials useable alone or in combination in cannula body 105 include, but are not limited to, polymers, metals, metal alloys, or composites or combinations thereof.

Examples of metals and metal alloys that may be useable in cannula body 105 include, but are not limited to, stainless steel, such as 304V, 304L, and 316L stainless steel; MP35-N (having a composition of about 35% Ni, 35% Co, 20% Cr, 100/Mo); a nickel-titanium alloy such as a superelastic (i.e. pseudoelastic) or linear elastic nitinol (having a composition of, for example, about 50% Ni, 50% Ti); nickel-chromium alloy; nickel-chromium-iron alloy; cobalt alloy; tungsten or tungsten alloys; tantalum or tantalum alloys, gold or gold alloys, and the like including any or other suitable metals, or combinations of metals, or alloys thereof which have sufficient strength and are biocompatible with living tissue. In some embodiments, it may also be desirable to use metals, or metal alloys that are suitable for metal joining techniques such as welding, soldering, brazing, crimping, friction fitting, adhesive bonding, etc. in order to combine materials or to attach cannula body 105 to other structures.

Examples of polymeric materials that may be useful in constructing the illustrated embodiment as well as other embodiments of cannula body 105 include polyaramides, polymethylpentenes, polysulfones, polycarbonates, polyesters, acrylates, polyamides, polyetheretherketones, modified phenylene oxides, polyetherimides, and other suitable polymeric materials that are biocompatible with living tissue, have low toxicity, and can be formed into suitable shapes in useful sizes with the structural integrity required to penetrate or excise living tissue.

Where polymeric materials are used, various marking regions may also be included to aid in navigating cannula body 105 to the proper location in the patient's body such as. For example, dots or bands of barium sulfate manufactured into cannula body 105 or added as part of cannula body 105, or added as an additional layer on the outside of cannula body 105 or the inside of cannula lumen 206. These marking regions may be useful in imaging cannula body 105 using various x-ray imaging techniques to aid physicians in guiding cannula body 105 into position. Similarly, cannula body 105 may include one or more echogenic markers such as metal flakes or rings formed as part of cannula body 105, or added to an inside or outside surface of cannula body 105. These echogenic markers may be useful in positioning cannula body 105 in a patient's body with the aid of unltrasonic imaging devices. Other types of imaging or marking devices may be included as well where it is advantageous to do so.

Similarly, some embodiments of cannula body 105 may have other cross sections such as ovular, rectangular, triangular and the like, or may be non-uniform such as, for example, substantially round throughout some regions of cannula body 105 while ovular in others. Other cross sections, or non-uniform cross sections may provide specific control over the extent to which cannula body 105 can bend or flex, and in what direction.

Cannula body 105 may be of various sizes depending on the application. For example, in one embodiment, cannula 102 includes an 18 gauge cannula body 105 having an outside diameter of about 0.05 inches and a lumen width 209 or inside diameter of about 0.042 inches resulting in a cannula body wall 203 about 0.008 inches thick. Various other sizes are envisioned as well including a larger cannula body 105 for extracting larger tissue samples having, for example, a 10 gauge cannula body 105 with an outside diameter of about 0.134 inches and an inner diameter or lumen width 209 of about 0.106 inches with a cannula body wall 203 of about 0.028 inches. Biopsy instrument 100 might also be configured for taking smaller tissue samples having a 30 gauge cannula body 105 with an outside diameter of about 0.01225 inches, a lumen width 209 of about 0.006250 inches, and a cannula body wall 203 about 0.006 inches thick. These represent only three examples, however, any other suitable arrangement of lumen width 209 and outside diameter may be used as well. Cannula 102 may, for example, be sized with a 12, 15, 20, 23, 25, or other suitable gauge cannula body 105.

Besides various diameters, cannula body 105 may also be constructed having varying cannula body lengths 106. For some applications, cannula body length 106 may be only about 10 inches long or even less while in other embodiments, cannula body length 106 may be about 24, 26, 30, or more inches long depending on various factors such as the location of the tissue to be collected.

Flexing region 115 has a flexing region length 116 as well which comprises some or all of cannula body length 106. In the illustrated embodiment, only one flexing region 115 is included, however, one or more such flexing regions may be advantageous and are envisioned as well. For example, in one embodiment of biopsy instrument 100, flexing region 115 covers all of cannula body 105 making flexing region length 116 and cannula body length 106 about equal in length and the ratio between cannula body length 106 and flexing region length 105 about 1 to 1. In another embodiment, flexing region length 116 is about 2.4 inches in length, while cannula body length 106 is about 24 inches in length making the ratio of cannula body length 106 to flexing region 116 about 10 to 1. Other ratios are envisioned as well, such as a first flexing region with a first ratio of cannula body length 106 to flexing region length 116, and one or more other flexing regions having second, third, and other subsequent ratios which may be equal to the first ratio, or larger or smaller than the first ratio.

Flexing region 115 may be somewhat more flexible than the rest of cannula body 105 by the inclusion of one or more slits 117 also shown in FIG. 2. In the illustrated embodiment, slits 117 include through-holes extending through cannula body wall 203 from an outer surface 211 of cannula body 105 into cannula lumen 206. In another embodiment, slits 117 extend 5%, 10%, 25%, 50%, 75% or more into cannula body wall 203 from outer surface 211 without penetrating into cannula lumen 206. The structural integrity of cannula body 105 may be maintained by the remaining wall portions 118 interspersed between the slits 117.

The pattern created by the slit or slits 117 and wall portions 118 is preferably arranged to provide for increased flexibility while reducing the likelihood of kinking cannula body 105 and binding between elongate cannula body 105 and stylet 123 regardless of the direction cannula body 105 is bent. In the illustrated embodiment, both flexibility and structural integrity are provided for by arranging the slits 117 and wall portions 118 in a generally helical slit pattern 119 with slits 117 (and wall portions 118) disposed circumferentially around and longitudinally along elongate cannula body 105. Slit pattern 119 is formed by this arrangement of slits 117 and wall portions 118 where adjacent slits are displaced both axially or longitudinally along cannula body 105 as well as radially or circumferentially around cannula body 105. In other embodiments, slit pattern 119 may include a single slit having one ore more discontinuities 117 in cannula body wall 203 separated by wall portions 118 arranged along one or more turns like those shown in greater detail in FIGS. 3 through 6. With the slits or discontinuities 117 arranged in a generally helical slit pattern 119, stresses on cannula body 105 caused by bending the device around sharp corners are distributed more evenly along cannula body wall 203 throughout the deflected portion of flexing region 115. The distribution of stresses may be further aided by embodiments of slit pattern 119 where the slits 117 in adjacent turns around cannula body 115 are disposed to include radially offset wall portions 118. Further detail on this aspect is illustrated in FIGS. 3 through 6 and described below.

Considering stylet 123 in further detail, stylet 123 operates as a tissue collector and in the illustrated embodiment in FIGS. 1 and 2 it is coaxially receivable within cannula 102 and may be extended or retracted longitudinally in a distal direction from within cannula 102 through a distal port 112. Stylet 123 has an elongate collector body 125 defining a tissue receiving opening or specimen notch 128 for receiving and maintaining the tissue sample or specimen of interest from the patient. Stylet 123 has a collector distal end 130 which may also include a penetrating member 131 positioned at the collector distal end 130.

Similar to cannula body 105, elongate collector body 125 may be constructed using a variety of materials and structures. Collector body 125 may be a unitary structure constructed of a single material, or of multiple materials joined together in any suitable manner. Likewise, collector body 125 as illustrated in FIG. 2 has a solid cross-section, but may also be of tubular construction defining one or more lumens within collector body 125. Some embodiments of collector body 125 may include both solid and tubular construction as well. Elongate collector body 125 may also have a collector body width 214 that is substantially uniform throughout the major portion of its length. Some examples of suitable materials useable alone or in combination in collector body 125 include, but are not limited to, polymers, metals, metal alloys, or composites or combinations thereof.

Both cannula body 105 and collector body 125 may be constructed of the same material, or of different materials. For example, many of the metals and metal alloys that may be useable in constructing cannula body 105 may also be used in constructing collector body 125.

Examples include, but are not limited to, those metals and metal alloys listed above including, MP35-N, nickel-titanium alloys such as various types of nitinol, gold or gold alloys, nickel-chromium alloys; nickel-chromium-iron alloys, cobalt alloys, tungsten or tungsten alloys, tantalum or tantalum alloys, which have sufficient strength and are biocompatible with living tissue. In some embodiments, it is desirable to use metals, or metal alloys that are suitable for metal joining techniques such as welding, soldering, brazing, crimping, friction fitting, adhesive bonding, etc.

Similarly, collector body 125 may also be formed of polymeric materials like those discussed above with respect to cannula body 105 including polyaramides, polycarbonates, polyesters, acrylates, polyamides, polyetheretherketones, modified phenylene oxides, polyetherimides, polymethylpentenes, polysulfones, and other suitable polymeric materials that are biocompatible with living tissue, have sufficiently low toxicity, and can be formed in suitable shapes and sizes with the structural integrity required to penetrate or excise tissue. Various marking regions may also be included on or manufactured into collector body 125 as described above for use along with x-ray or ultrasonic imaging to aid in positioning collector body 125.

As discussed briefly above, cannula 102 and stylet 123 can cooperate to excise a tissue sample from a patient. To facilitate the biopsy procedure (discussed in further detail below with respect to retrieving a sample from the liver and FIGS. 7A and 7B), biopsy instrument 100 includes an actuating assembly 133 coupled to the proximal end 107 of cannula 102 that includes a first grip 134 and a second grip 135. An actuator 137 is coupled to the elongate collector body 125 of tissue collector 123 while first grip 134 and second grip 135 are coupled to elongate cannula body 105 of cannula 102. In one embodiment, manipulating actuator 137 and grips 134 and 135 longitudinally parallel to cannula body 105 causes stylet 123 to advance or retract from within cannula lumen 209 through distal port 112. Using this embodiment, the actuator 137 can be pulled proximally relative to cannula body 105 causing stylet 123 to retract into cannula lumen 209 thus protecting the patient from the risk of injury caused by penetrating member 131. Cannula body 105 can then be advanced through the patient's body, such as through vasculature of sufficient size, until the site is reached. Cannula body 105 may then be positioned near the biopsy site, such as directly adjacent to the tissue from which the specimen is to be excised, and the stylet 123 advanced into the tissue by holding cannula body 105 in place using grips 134 and 135 and pressing distally on actuator 137. The tissue specimen naturally presses inward around stylet 123 causing the tissue specimen to enter the tissue receiving opening 128. Actuator 137 is then held in place while cannula body 105 is pressed forward using grips 134 and 135. The distal movement of the cannula body 105 relative to stylet 123 causes prolapsed tissue in the tissue receiving opening 128 to be excised by cutting surface 111 separating the sample from the remaining tissue in the patient. Biopsy instrument 100 is then withdrawn from the patient and the tissue sample retrieved from the tissue receiving opening 128.

Various other embodiments of actuating assembly 133 are envisioned as well including various systems and devices and the like such as the multiple biopsy gun disclosed in U.S. Pat. No. 5,595,185 herein incorporated by reference, the handheld biopsy device disclosed in U.S. Pat. No. 8,206,409 herein incorporated by reference, or the automated biopsy instrument disclosed in U.S. Pat. No. 5,779,647 herein incorporated by reference as well. Similarly, tissue receiving opening 128, cutting surface 111, and actuating assembly 133 may also be configured to rotate stylet 123 or cannula body 105 rather than slide cannula body 105 like the apparatus for obtaining a biopsy sample disclosed in published U.S. patent application 2012/0245487 herein incorporated by reference. Any suitable system or device for moving catheter body 105 or stylet 123 (or both) relative to one another to excise tissue is envisioned and represented in FIG. 1 and FIG. 7A by actuating assembly 133.

As discussed above, the generally helical slit pattern 119 illustrated in FIG. 1 is created by the disposition of slits 117 and wall portions 118. Further details and examples of how slit pattern 119 may be organized within flexing region 115 are illustrated in FIGS. 3 through 6. Slits 117 and wall portions 118 are arranged in one or more turns 302. Slits 117 have a slit length 313 and a slit width 309. Wall portions 118 have a wall portion length 315, or, put another way, discontinuities (slits 117) in the cannula body wall are spaced apart by a spacing length 315. Turns 302 are separated by a longitudinal offset 306. Slits 117 are positioned along a slit are 325 which may be considered as referring to that portion of a perimeter 304 of cannula body wall 203 that defines a particular slit 117 within a given turn 302. Perimeter 304 can also be thought of as a circumference 304 in those embodiments where cannula body 105 is generally circular or ovular. Similarly, wall portions 118 occupy those portions of perimeter or circumference 304 between slits 117 and are therefore also disposed along wall portion arcs 327. In order to illustrate various embodiments of these dimensions, FIGS. 3 through 6 illustrate flexing region 115 by flattening a segment of slit pattern 119 as if elongate cannula body 105 had been cut longitudinally along its long axis opened. Thus perimeter 304 in FIGS. 3 through 6 represents one full 360 degree rotation about the circumference or perimeter of elongate cannula body 105, while lateral displacement in FIGS. 3 through 6 indicates axial displacement longitudinally along a portion of elongate cannula body 105 toward proximal end 107 or distal end 109. Thus, in the preferred embodiment where elongate cannula body 105 has a substantially circular or ovular cross section, one end of circumference 304 can be thought of as 0 degrees, while the opposite end as 360 degrees.

Throughout FIGS. 3 through 6, reference lines A through H are positioned to aid in the discussion of the various embodiments. Reference lines A and B generally indicate the radial extents of a slit 117A, while lines C and D generally show the radial extent of the next slit or discontinuity in the progression 117B, and so forth. Similarly, the radial extents of the wall portions interspersed between the slits 117 are generally indicated by the same reference lines. For example, the radial extent of wall portion 118A is generally indicated by lines B and C, wall portion 118B is generally indicated by lines D and E, and so forth.

Figure 3:
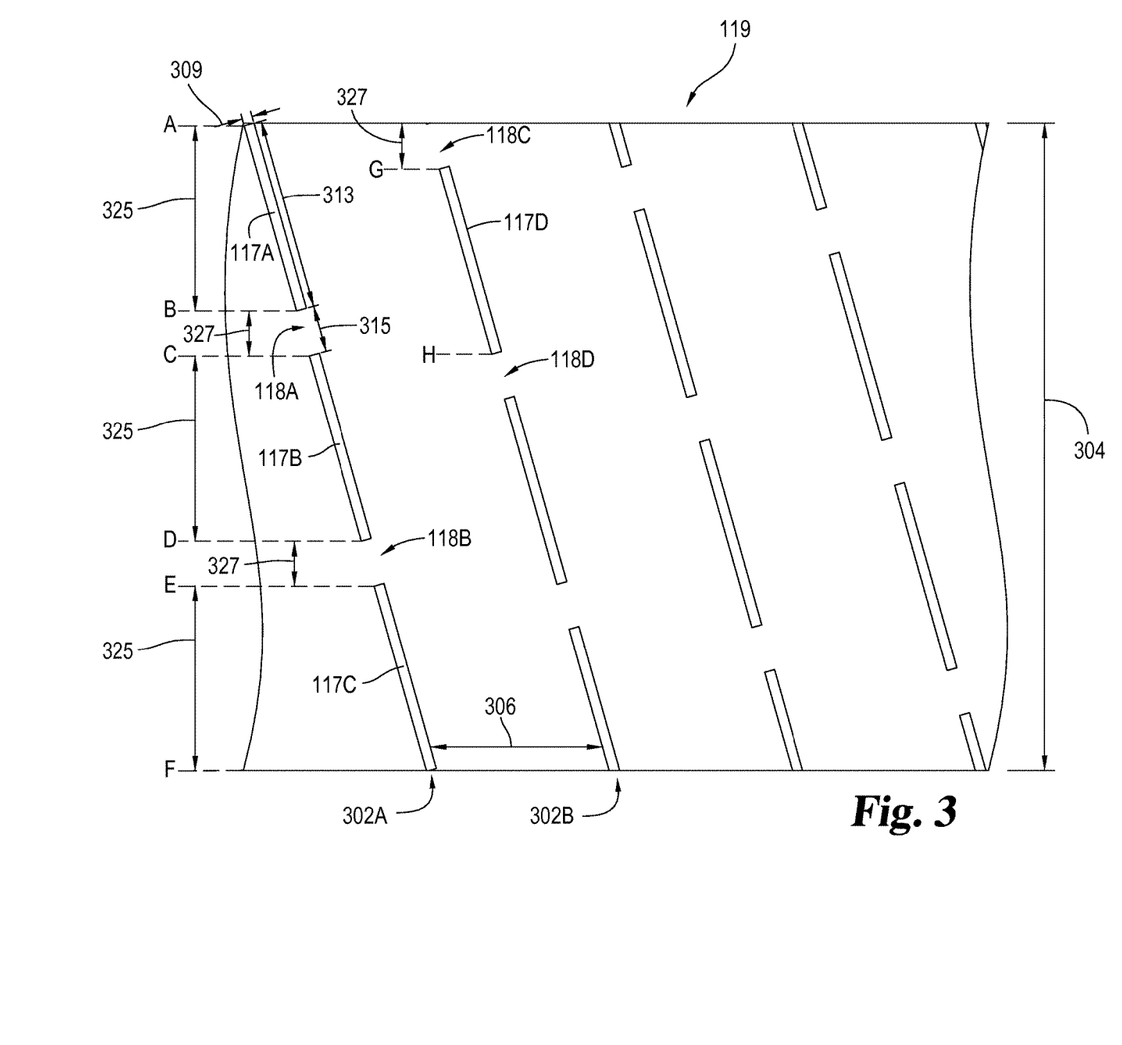
FIG. 3 is a diagrammatic view of one embodiment of the generally helical slit pattern shown in FIG. 1.

Considering the embodiment of slit pattern 119 illustrated in FIG. 3 in further detail, several turns of slit pattern 119 are shown. In this embodiment, slit arc 325 and wall portion arc 327 are substantially uniform throughout the pattern resulting in a slit length 313 and a wall portion length 315 that is also substantially uniform throughout slit pattern 119. As previously noted, line A can be thought of as a reference location at 0 degrees around circumference 304, while reference line F can be thought of as a reference location at 360 degrees. Thus A and F can indicate the same radial location along circumference 304 and are both included in FIG. 3 for consistency with respect to FIGS. 4 through 6 to aid in the following description.

It can therefore be appreciated that reference lines A and B generally indicate the radial extent of slit arc 327 and slit 117A as being about 103 degrees apart around the circumference 304, while reference lines B and C generally indicate the radial extent of wall portion 118A as being about 25 degrees apart in the embodiment illustrated in FIG. 3. It can also be appreciated from FIG. 3 that in this embodiment of the generally helical slit pattern 119, at least some part of wall portions 118 (as well as slits 117) are radially offset from wall portions in adjacent turns 302. For example, wall portion 118A in turn 302A is disposed along an arc beginning at B at about 103 degrees and ending at C at about 128 degrees. By contrast, wall portion 118C in adjacent turn 302B is radially offset from 118A by at least 75 degrees as it is positioned on an arc extending between A (or F) and G, that is between about 0 degrees and about 25 degrees. Similarly, wall portion 118D is radially offset from wall portion 118A by as much as about 25 degrees as 118D is positioned on an arc extending between about 128 degrees and about 153 degrees. Radially offsetting the wall portions can provide strength while also further reducing the chance of cannula body 105 kinking, pinching, or otherwise losing structural integrity during use and thus binding on stylet 123 possibly reducing the effectiveness of biopsy instrument 100.

Figure 4:
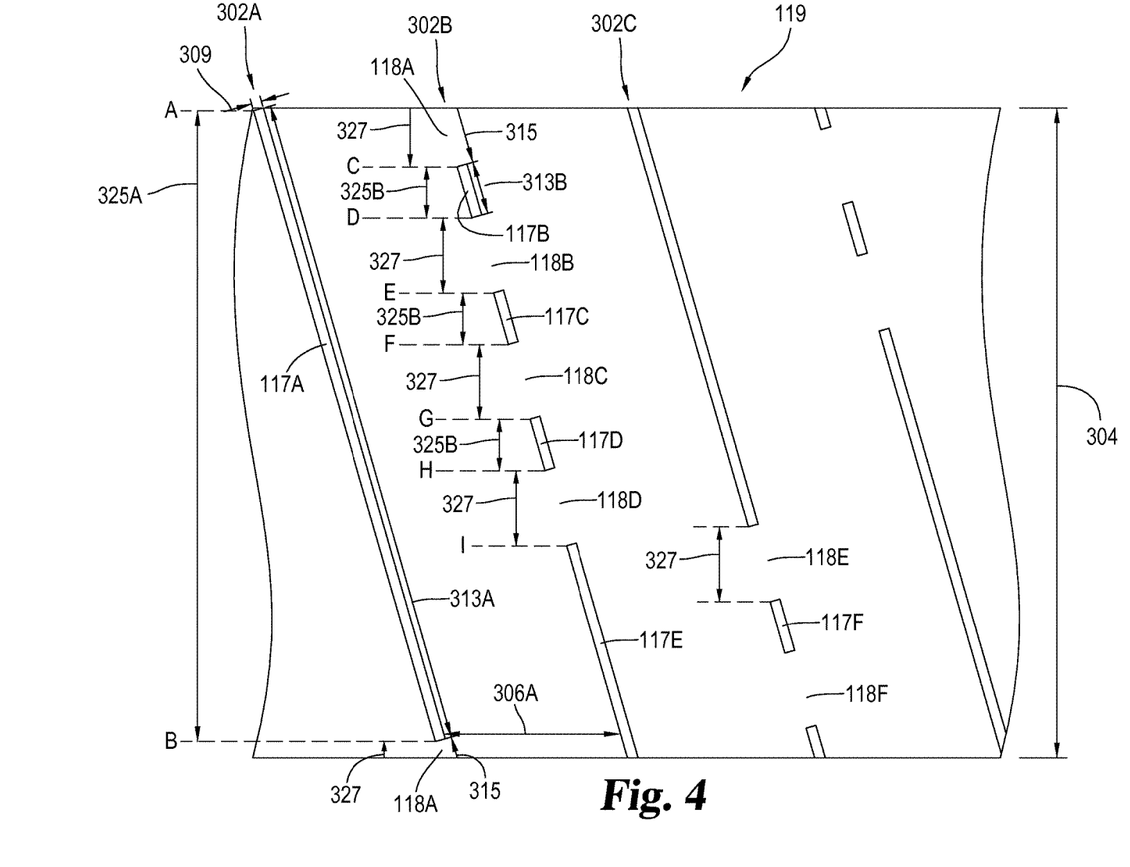
FIG. 4 is a diagrammatic view of another embodiment of the generally helical slit pattern shown in FIG. 1.

A second embodiment of a generally helical slit pattern 119 is illustrated in FIG. 4 and uses similar notation discussed above to indicate the dimensions for a slit pattern 119 having slits with lengths that are not substantially uniform, but with wall portions whose lengths are substantially uniform. In FIG. 4, slit 117A extends along an arc from A to B as in FIG. 3, except in the case of the embodiment illustrated in FIG. 4, the arc from A to B extends from about 0 degrees to about 350 degrees around the circumference or perimeter 304 of cannula body 105. This yields a slit length 313A that is substantially longer than the slit length 313B of slits 117B through 117D and 117F which are disposed along arcs of about 30 degrees. Wall portions 118A through 118F, as well as the unmarked wall portions shown in slit pattern 119 are substantially uniform in length because the arcs between B and C, D and E, F and G and so forth are substantially uniform and about 40 degrees. Thus B to C represents an arc extending from about 350 degrees along turn 302A to about 30 degrees along turn 302B while D to E represents a similar sized arc extending from about 60 degrees to about 100 degrees along turn 302B. As with FIG. 3, turns 302A and 302B are axially or longitudinally offset along cannula body 105 by a longitudinal offset 306 that is substantially uniform throughout slit pattern 119. Also like the embodiment in FIG. 3, it can be appreciated from FIG. 4 that at least some part of wall portions 118 (as well as slits 117) are radially offset from wall portions in adjacent turns 302. For example wall portion 118D is arranged along the arc starting at H at about 200 degrees and extends about 30 degrees around the circumference or perimeter 304 of cannula body 105 to about 240 degrees along turn 302B. Slit 117E thus extends from about 240 degrees on turn 302B to about 230 degrees along turn 302C thus defining a wall portion 118E from about 230 degrees to about 270 degrees. Thus wall portions 118D and 118E in adjacent turns are at least partially radially offset with partially overlapping wall portion arcs 327.

Figure 5A:
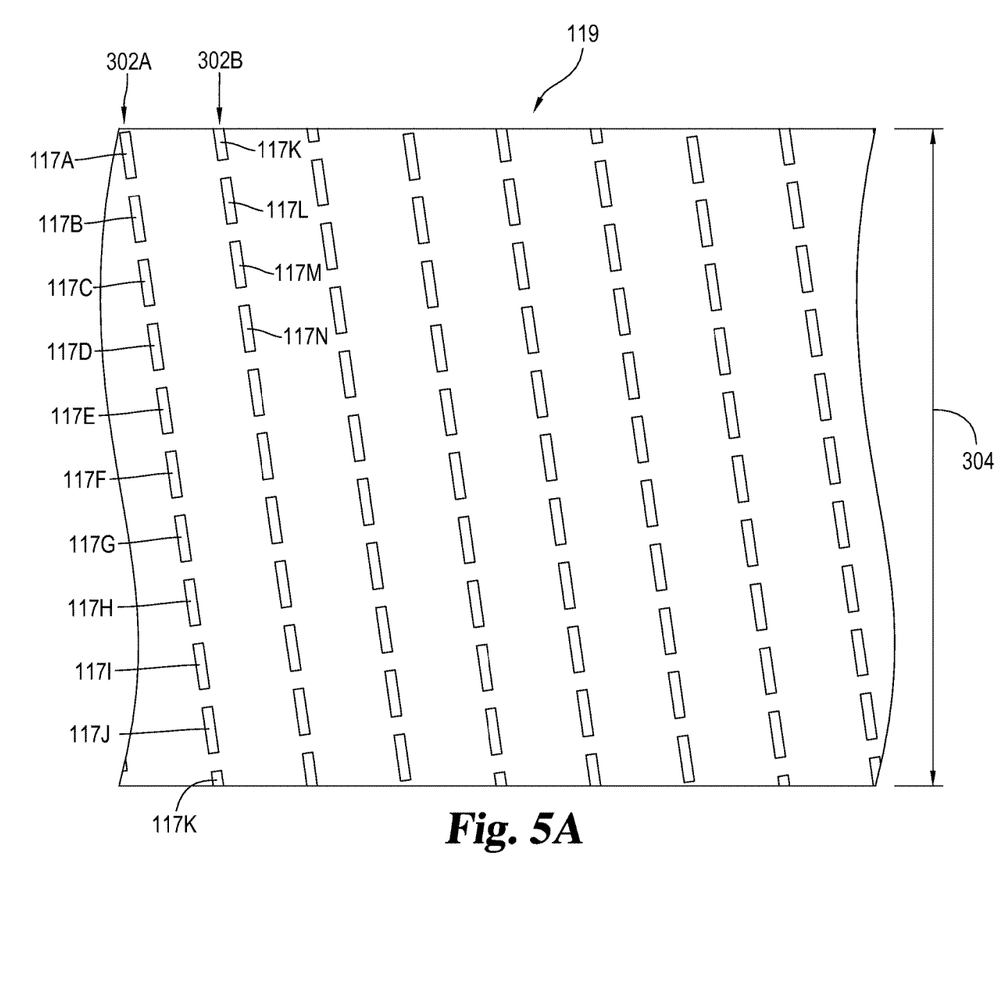
FIG. 5A is a diagrammatic view of another embodiment of the generally helical slit pattern shown in FIG. 1.
Figure 5B:
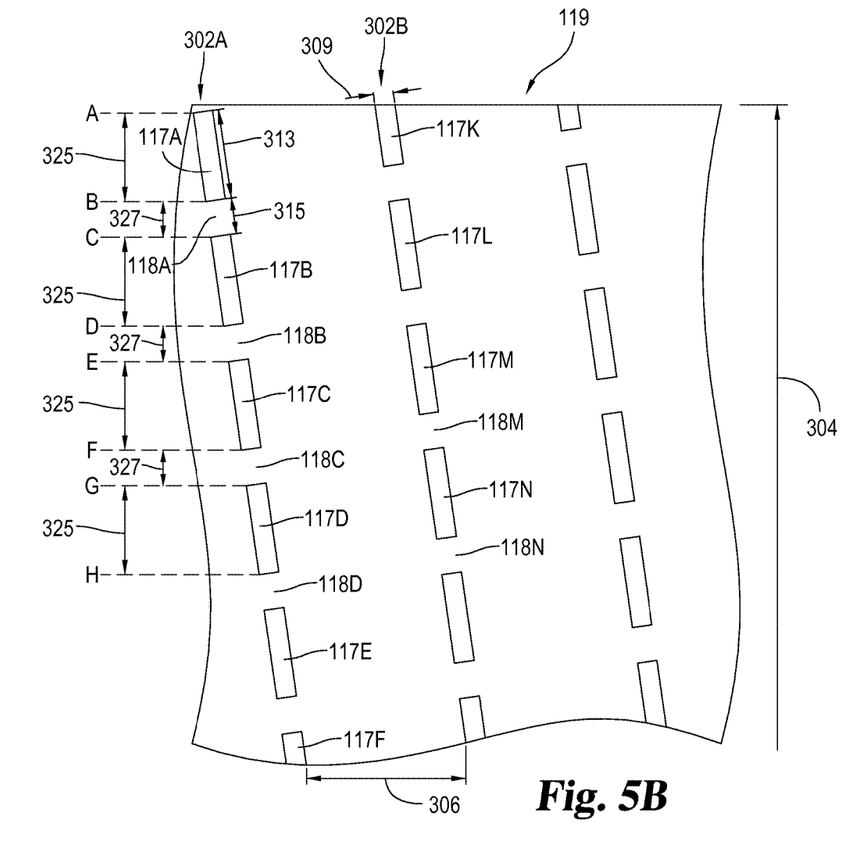
FIG. 5B is a diagrammatic view illustrating further detail of the generally helical slit pattern shown in FIG. 5A.

A third embodiment of generally helical slit pattern 119 is illustrated in FIG. 5A and in further detail in FIG. 5B. In this embodiment, slit pattern 119 has substantially uniform slits 117 and wall portions 118 having a similar arrangement as discussed with respect to FIGS. 3 and 4 using similar notation. In this example, slit arc 325 is shown as extending about 25 degrees around circumference 304 of cannula body 105 and wall portion arc 327 is also substantially uniform extending about 10 degrees around circumference 304. Slits 117 have a length 313 and a width 309 as in previous examples, and wall portions 118 have a length 315 as well. As in previous examples, at least some of wall portions 118 in turn 302B are radially offset from wall portions in turns 302A. For example, wall portion 118C extends along an arc from about 95 to about 105 degrees in turn 302A while wall portion 118M in adjacent turn 302B, as in previous examples, appears on a different part of the circumference 304 being disposed along an arc that extends from about 85 to about 95 degrees around circumference 304.

Figure 6:
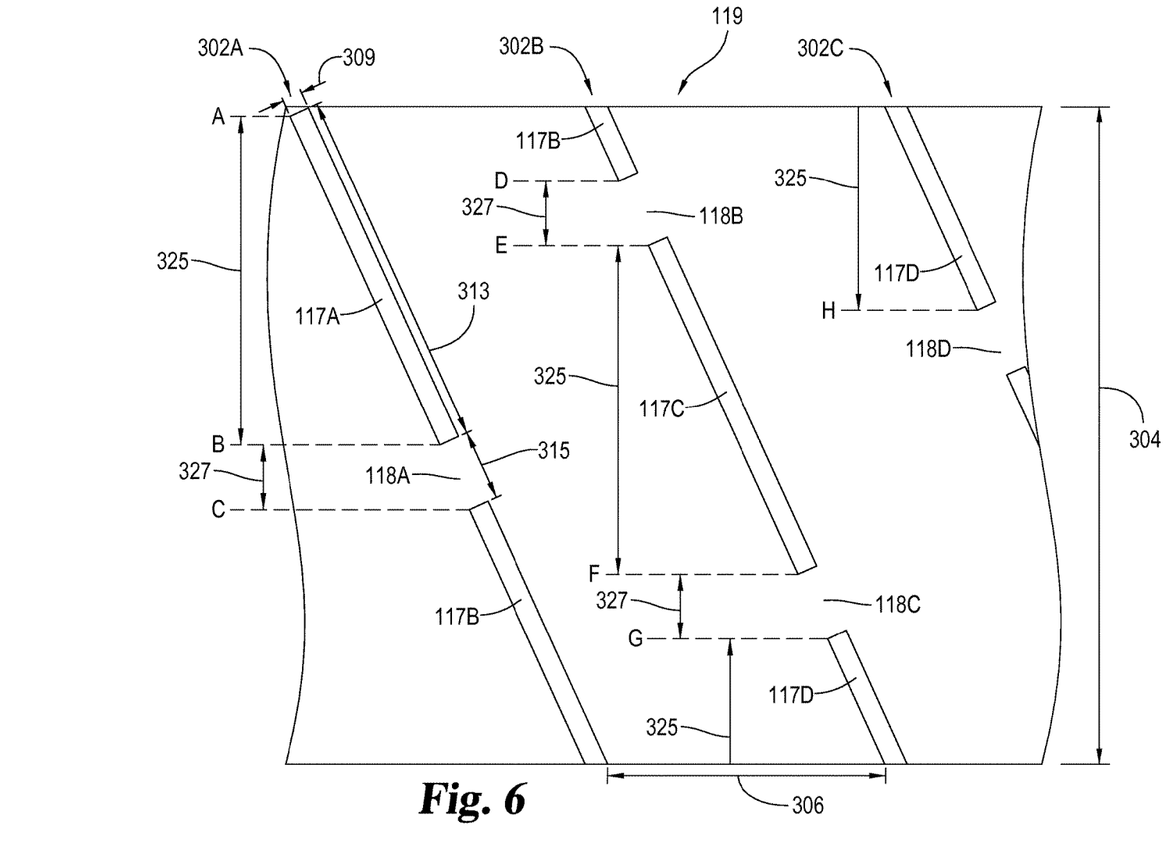
FIG. 6 is a diagrammatic view of another embodiment of the generally helical slit pattern shown in FIG. 1.
Figure 7A:
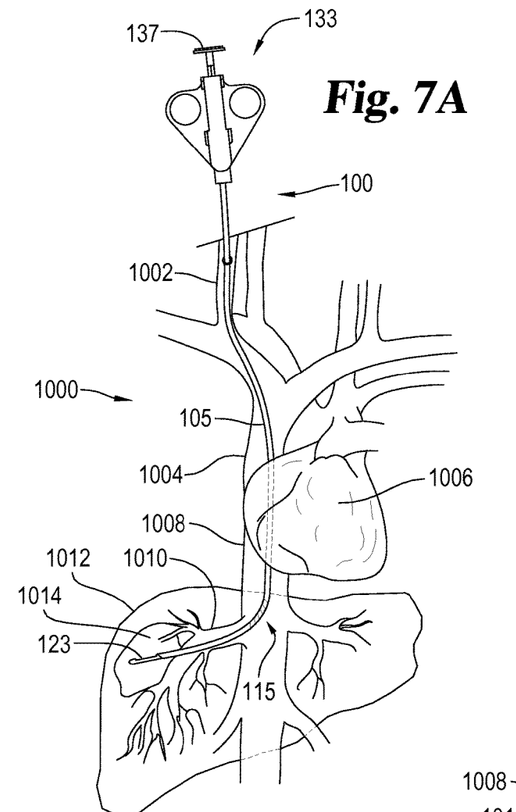
FIG. 7A is a diagrammatic view illustrating one example of how the biopsy instrument of FIG. 1 might be used to excise a tissue sample.
Figure 7B:
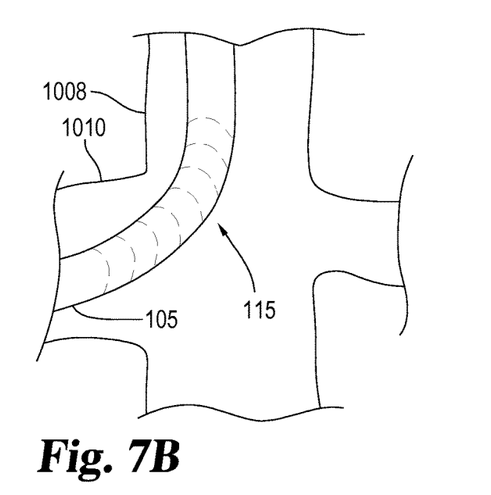
FIG. 7B is a diagrammatic view illustrating further detail of the positioning of the biopsy instrument shown in FIG. 7A.

Another embodiment of slit pattern 119 is illustrated in FIG. 6 similar to the patterns illustrated in FIGS. 3 through 5B having slits 117 and wall portions 118 of substantially uniform lengths and widths and positioned along slit arcs 325 extending about 180 degrees, and wall portion arcs 327 extending about 35 degrees and arranged in turns 302A through 302C. In this example, it may be noted that slit width 309 is wider than in previous examples, while longitudinal offset 306 is also larger than the in previous examples. No particular limitation should be implied on slit width 309 from any of the illustrated embodiments. As with the slit length 313, the slit width 309 may be uniform or varied throughout slit pattern 309, and the dimensions may be of any size suitable for use with biopsy device 100.

As in previous examples, wall portions 118 in adjacent turns are at least partly radially offset from one another, such as, for example wall portion 118A in turn 302A extends from about 180 degrees to about 215 degrees, while wall portions 118B and 118C are disposed along turn 302B from about 35 degrees to about 70 degrees and from about 250 degrees to about 285 degrees respectively. In both cases, wall portions 118B and 118C are radial offset, that is, they are positioned along different wall portion arcs 327 that do not radially coincide in adjacent turns 302A and 302B.

Although several examples of a generally helical slit pattern 119 are shown in FIGS. 3 through 6, numerous other variations are envisioned as well. For example, it should not be assumed from FIGS. 3 through 6 that slit width 309 must be uniform throughout slit pattern 119, although this may be preferred for various reasons such as ease of manufacturing. Similarly, the lengths and widths of slits 117 and wall portions 118 may be varied within slit pattern 119 as well to increase or decrease flexibility in one direction, or in all directions equally. Likewise, slits 117 are illustrated as rectangular in shape, but may be formed in any suitable geometry such as ovals, circles, squares, rounded rectangles, or complex polygons including any suitable combination of lines, curves, arcs, and the like. Slits 117 may be smaller than those shown in FIG. 3, such as those shown in FIGS. 5A and 5B, or larger such as those shown in FIGS. 4 and 6. Various combinations of lengths and widths of slits 117 and wall portions 118 may be included in the same slit pattern 119, and the longitudinal spacing between turns 302 may be varied as well. These and various other suitable combinations are therefore also envisioned. Similarly, turns 302 within slit pattern 119 may be closer together as shown in FIGS. 5A and 5B, or farther apart as illustrated in FIG. 6 then turns 302 shown in FIGS. 3 and 4. No particular assumption or limitation should be imposed based on longitudinal offset 306 in this regard as any suitable offset 306 is considered. As with other dimensions and arcs noted above, although it may be advantageous to construct a slit pattern 119 with a longitudinal offset 306 between turns 302 that is substantially uniform throughout the pattern, such a requirement is not necessary as it may be advantageous to the performance of biopsy instrument 100 to include in pattern 119 a non-uniform longitudinal offset 306 in some situations.

The exemplary embodiments shown may be constructed using any suitable machine, technique, system, or method such as, for example, by laser cutting slits 117 into the cannula body wall 203. Such techniques may be used to manufacture slit pattern 119 with a cannula body wall 203 having a broad range of lumen widths 209 and perimeters or circumferences 304. For example, in one embodiment, the slits 117 are about 0.002 inches wide meaning that for an 18 gauge cannula body 105 with an outside diameter of about 0.05 inches, and an inside diameter (lumen width 209) of about 0.042 inches, the ratio of lumen width 209 to slit width 309 is about 21 to 1. In other embodiments, slit width 309 might be a wide range of other suitable widths such as 0.001 inches, 0.004 inches or 0.005 or more depending on the size of cannula body 105. For example in a smaller biopsy instrument 100 with a 30 gauge cannula body 105 having an outside diameter of about 0.01225 inches and a lumen width 209 or inside diameter of about 0.00625 inches, a slit width 309 of about 0.002 inches yields a ratio of lumen width 209 to slit width 309 of about 3.13 to 1. This ratio drops to about 1.25 to one for slit widths of 0.005 inches. On the other hand, in another example of a larger instrument 100 having a 10 gauge cannula body the ratio of lumen width 209 to slit width 309 varies from about 53 to 1 for a slit width of 0.002, to about 21 to 1 for a slit width of 0.005 inches. Any other suitably sized cannula having any useful slit width may be used together as well.

On a related note, the various embodiments shown exhibit a range of ratios of lumen width 209 to slit length 313. For example, in FIG. 3 is shown one embodiment of slit pattern 119 having a slit arc of about 103 degrees, and a wall portion arc of about 25 degrees. If, for example, the longitudinal offset 306 is about 0.012 inches between turns 302, then slits 117 have a length of about 0.0452 inches and a wall portion length 315 of about 0.0109 inches in this embodiment of slit pattern 119. In the case of an 18 gauge cannula body 105 with the dimensions given above, the ratio of lumen width 209 to slit length 313 is about 0.93 to 1 and the ratio of lumen width 209 to wall portion length 315 is about 3.84 to 1. Similar ratios for a larger cannula such as a 10 gauge cannula body 105 with the dimensions given above make the ratio of lumen width 209 to slit length 313 about 0.88 to 1 and the ratio of lumen width 209 to wall portion length 315 about 3.62 to 1. For a smaller cannula such as the 30 gauge cannula body 105 with the dimensions given above, the ratio of lumen width 209 to slit length 313 about 0.54 to 1 and the ratio of lumen width 209 to wall portion length 315 is about 2.23 to 1. These are but a few examples of the wide range of ratios between lumen width 209 and slit length 313 and wall portion length 315. Numerous other sizes of cannula bodies 105 may be used yielding various other ratios as well.

Other examples are illustrated, such as in FIG. 4 where at least two different slit lengths 313A and 313B are shown separated by substantially uniform wall portions 118 with a wall portion length 315. Slit 117A has a slit arc 325A as shown of about 350 degrees and a wall portion arc 327 of about 40 degrees. For an 18 gauge cannula body 105 with the dimensions given above having turns 302 spaced about 0.012 inches apart, this configuration yields a slit length 313A of about 0.153 inches and a wall portion length 315 of about 0.0175 with a ratio of lumen width 209 to slit length 313A of about 0.27 to 1 and a ratio of lumen width 209 to wall portion length 315 of about 2.4 to 1. For a larger cannula body 105 such as a 10 gauge body with the dimensions given above, the slit length 313A is about 0.409 inches and a wall portion length 315 is about 0.0468 inches with a ratio of lumen width 209 to slit length 313A of about 0.26 to 1 and a ratio of lumen width 209 to wall portion length 315 of about 2.27 to 1. For a smaller cannula body

105 such as a 30 gauge body of the dimensions given above, slit length 313A is about 0.039 inches long and a wall portion length is about 0.004 inches with a ratio of lumen width 209 to slit length 313A of about 0.16 to 1 and a ratio of lumen width 209 to wall portion length 315 of about 1.4 to 1. Slits 117 disposed along slit arcs 325B of about 30 degrees would have dimensions similar in size, though smaller, than the wall portion lengths 315 which are positioned along an arc of about 40 degrees. Once again, various other cannula sizes may be used as well, yielding other ratios greater or smaller than these depending on the relative sizes.

FIGS. 5A and 5B illustrates a pattern 119 of smaller slits 117 and narrower wall portions 118 that are also positioned along turns 302 that are disposed closer together than in previous patterns 119 shown in FIGS. 3 and 4. Slits 117 in FIG. 5B are illustrated with a slit arc 325 as shown of about 25 degrees and a wall portion are 327 of about 10 degrees. For an 18 gauge cannula body 105 with the dimensions given above having turns 302 with a longitudinal offset of about 0.006 inches apart, this arrangement yields a slit length of about 0.0109 inches and a wall portion length 315 of about 0.0044 inches with a ratio of lumen width 209 to slit length 313 of about 3.85 to 1 and a ratio of lumen width 209 to wall portion length 315 of about 9.62 to 1. For a larger cannula body 105 such as a 10 gauge body with the dimensions given above, slit length 313 is about 0.0292 inches and wall portion length 315 is about 0.0117 inches with a ratio of lumen width 209 to slit length 313 of about 3.63 to 1 and a ratio of lumen width 209 to wall portion length 315 of about 9.06 to 1. For a smaller cannula body 105 such as a 30 gauge body of the dimensions given above, slit length 313 is about 0.0027 inches and wall portion length 315 is about 0.0018 inches with a ratio of lumen width 209 to slit length 313 of about 2.31 to 1 and a ratio of lumen width 209 to wall portion length 315 of about 5.78 to 1. Once again, various other cannula sizes may be used as well, yielding other rations greater or smaller than these depending on the relative sizes.

FIG. 6 illustrates a pattern 119 of wider slits 117 spaced further apart than, for example, those shown in FIG. 3. Slits 117 in FIG. 6 are illustrated with a slit arc 325 of about 180 degrees and a wall portion arc 327 of about 35 degrees. Using, for example, an 18 gauge cannula body 105 with the dimensions given above having turns 302 with a longitudinal offset 306 of about 0.024 inches, this embodiment yields a slit length of about 0.0795 inches and wall portion length 315 of about 0.0154 inches with a ratio of lumen width 209 to slit length 313 of about 0.53 to 1 and a ratio of lumen width 209 to wall portion length 315 of about 2.72 to 1. For a larger cannula body 105 such as a 10 gauge body with the dimensions given above, the slit length 313 is about 0.2108 and wall portion length 315 is about 0.04099 inches with a ratio of lumen width 209 to slit length 313 of about 0.5 to 1 and a ratio of lumen width 209 to wall portion length 315 of about 2.59 to 1. For a smaller cannula body 105 such as a 30 gauge body of the dimensions given above, slit length 313 is about 0.0227 inches and wall portion length 315 is about 0.0044 inches with a ratio of lumen width 209 to slit length 313 of about 0.28 to 1 and a ratio of lumen width 209 to wall portion length 315 of about 1.42 to 1. Once again, various other cannula sizes may be used as well, yielding other rations greater or smaller than these depending on the relative sizes.

It can be appreciated from the various embodiments illustrated and described above, as well as from the exemplary dimensions given, that the generally helical slit pattern 119 may include one or more turns 302 having one or more slits 117 and wall portions 118 of varying lengths and widths with a uniform or varying longitudinal offset 306 between turns 302. Longitudinal offset 306 is preferably between about 0.005 inches and 0.03 inches and most preferably about 0.012 inches, although any other suitable longitudinal offset 306 may be used as well. Likewise, depending on the slit arc 325 (or arcs where the arc 325 varies across slit pattern 119), and the wall portion arc 327 (or wall portion arcs), the ratio of lumen width 209 to slit length 313 preferably various from about 0.2 to 1 to about 4 to 1, and that there may be suitable combinations of cannula 105, slits 117, and wall portions 118 that fall outside this range as well. This is because slit lengths 313, as illustrated above, can vary significantly depending on various factors such as the slit are 325, the outside diameter of cannula body 105, and the longitudinal offset 306 between slits 117. Slit lengths 313 are preferably between about 0.004 inches to about 0.41 inches, although suitable embodiments of slit length 313 outside this range are envisioned as well.

Turning now to how biopsy instrument 100 can be used, one example of a method for taking a biopsy tissue sample from a patient 1000 is illustrated in FIGS. 7A and 7B. The process generally begins by a physician positioning biopsy instrument 100 within the patient. In FIG. 7A, biopsy instrument 100 is navigated through the vasculature of a patient around or through the heart 1006 to excise tissue from the area to be biopsied 1014 such as the liver 1012. Various techniques may be used optionally involving other devices where it is advantageous to do so, such as, for example, valves, introducer needles, wire guides, catheters, and the like, some of which are included in the following description.

One such technique for positioning biopsy instrument 100 and taking a tissue sample involves puncturing the right internal jugular vein 1002 with an access needle and inserting, for example, a wire guide through the needle into the jugular vein 1002 and removing the needle. An outer or guiding catheter may be introduced over the wire guide and manipulated through the superior vena cava 1004 and inferior vena cava 1008, and into the right hepatic vein 1010. Once the wire guide is seated in the right hepatic vein 1010, the guiding catheter may then be removed. Various other devices may also be assembled in preparation for introducing biopsy instrument 100 as well such as an introducer sheath, a stiffening cannula, a check valve adapter, or other similar devices. The physician may also inject contrast dye or use other suitable imaging techniques such as an ultra sound imaging system to verify the location and positioning within right hepatic vein 1010 of the devices inserted thus far.

The biopsy instrument 100 may then be advanced through or in conjunction with these devices until distal end 109 is positioned adjacent the tissue to be sampled, in this case in the liver 1012. Stylet 123 with penetrating member 131 can then be advanced beyond distal end 109 and into the liver tissue as shown in FIG. 7A. The physician maintains the position of the cannula 102 and advances stylet 123 by any suitable method including the various methods discussed above thus exposing the tissue receiving opening or specimen notch 128 within the area to be biopsied 1014. Biopsy instrument 100 is then "fired" or actuated using actuating assembly 133 as described above excising and capturing the tissue within the tissue receiving opening 128. The excised tissue sample can then be removed from the patient 1000 by withdrawing biopsy instrument 100.

The movement of stylet 123 within cannula body 105 can occur in spite of the sharp bend required to insert elongate cannula body 105 into right hepatic vein 1010 because of the pattern of slits and wall portions in flexing region 115 as shown in FIG. 7B. Biopsy instrument 100 may also be used in a similar manner to access tissue from other areas of a patient's body besides the liver, and may be used to collect tissue samples from any region of the body where it is advantageous to use do so.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A biopsy instrument, comprising:
    a cannula including:
        an elongate metal cannula body having a proximal end, a distal end, and a metal cannula body wall having an outer surface defining an outermost surface of the biopsy instrument and an inner surface defining a cannula lumen within the elongate cannula body, the cannula lumen having a lumen width;
        a cutting surface at the distal end of the elongate cannula body, said cutting surface extending from said outer surface of said cannula body to said inner surface of said cannula body;
        at least one flexing region having a plurality of slits defined by the cannula body wall and extending through the cannula body wall to form through openings from said outermost surface into the cannula lumen, and a plurality of wall portions extending between adjacent slits, wherein the plurality of slits are arranged in a helical slit pattern extending circumferentially around and longitudinally along the elongate cannula body, and wherein each of the individual slits has a slit width of 0.001 inches to 0.005 inches; and
    a tissue collector including:
        an elongate collector body coaxially receivable within the cannula lumen, the elongate collector body terminating in a tissue penetrating member, said tissue penetrating member having lateral sidewalls converging in a distal direction to a pointed leading end, wherein the pointed leading end is held centrally within the cannula lumen when the tissue penetrating member is received in the cannula lumen; and
        a tissue receiving opening defined by the elongate collector body and disposed near a collector distal end of the elongate collector body, and wherein the pointed leading end is at the collector distal end of the elongate collector body distal to the tissue receiving opening.

2. The biopsy instrument of claim 1:
    wherein the one or more slits and wall portions forming the helical slit pattern are arranged in a plurality of turns extending circumferentially around and longitudinally along the cannula body; and
    wherein adjacent turns include radially offset wall portions.

3. The biopsy instrument of claim 1, wherein the slit width of each of the plurality of slits is uniform.

4. The biopsy instrument of claim 1, wherein the circumferentially extending slits are offset longitudinally along the elongate cannula body by a uniform longitudinal spacing, and wherein the uniform longitudinal spacing is greater than the slit width of any one slit.

5. The biopsy instrument of claim 4, wherein the uniform longitudinal spacing is between 0.005 inches and 0.03 inches.

6. The biopsy instrument claim 1, wherein the circumferentially extending slits have a slit length that is uniform.

7. The biopsy instrument of claim 6, wherein the ratio of lumen width to slit length is between 0.2 to 1 and 4 to 1.

8. The biopsy instrument of claim 6, wherein the slit length is between 0.004 inches and 0.41 inches.

9. The biopsy instrument of claim 1, wherein the at least one flexing region has a flexing region length, the elongate cannula body has a cannula body length, and the ratio of the cannula body length to the at least one flexing region length is between 1 to 1 and 10 to 1.

10. A biopsy instrument, comprising:
    a first elongate body having a proximal port and a distal port, the first elongate body comprising a cannula body having a single-layer tubular construction comprising a cannula body wall having an outer surface defining an outermost surface of the biopsy instrument and an inner surface defining a lumen within the first elongate body, the lumen having a lumen width, the lumen in fluid communication with the proximal port and the distal port, the first elongate body also having a cutting surface;
    at least one flexing region defining a plurality of slits in the cannula body wall, the slits forming a helical slit pattern extending circumferentially around and longitudinally along the first elongate body and extending through the cannula body wall to form through openings from the outermost surface into the cannula lumen, wherein each of the individual slits has a slit width of 0.001 inches to 0.005 inches, and wherein the individual slits are separated by wall portions such that the plurality of slits and wall portions forming the helical slit pattern are arranged in a plurality of turns extending circumferentially around and longitudinally along the cannula body; and
    a second elongate body having a distal end, the second elongate body coaxially receivable within the lumen, the second elongate body having a tissue receiving opening and a tissue penetrating member distal to the tissue receiving opening, wherein lateral sidewalls of the tissue penetrating member converge to a leading point held in a spaced position from the inner surface of the first elongate body when the tissue penetrating member is received in the cannula lumen.

11. The biopsy instrument of claim 10: wherein adjacent turns of said helical slit pattern include radially offset wall portions.

12. The biopsy instrument of claim 10, wherein the slit width of each of the plurality of slits is uniform.

13. The biopsy instrument of claim 10, wherein the circumferentially extending slits are offset longitudinally along the first elongate body by a uniform longitudinal spacing, and wherein the uniform longitudinal spacing is greater than the slit width of any one slit.

14. The biopsy instrument of claim 13, wherein the uniform longitudinal spacing is between 0.005 inches 0.03 inches.

15. The biopsy instrument of claim 10, wherein the circumferentially extending slits have a slit length that is uniform.

16. The biopsy instrument of claim 15, wherein the ratio of lumen width to slit length is between 0.2 to 1 and 4 to 1.

17. The biopsy instrument of claim 15, wherein the slit length is between 0.004 inches and 0.41 inches.

18. The biopsy instrument of claim 10, wherein the at least one flexing region has a flexing region length, the first elongate body has a cannula body length, and the ratio of the cannula body length to the at least one flexing region length is between 1 to 1 and 10 to 1.

19. The biopsy instrument of claim 10, wherein the cutting surface is at a distal end of the first elongate body.

20. The biopsy instrument of claim 10, wherein the distal port is at a distal end of the first elongate body.

21. A method for taking a biopsy from a patient, comprising:
positioning a biopsy instrument according to claim 10 in a patient;
actuating the biopsy instrument;
removing the biopsy instrument from the patient.

22. The method of taking a biopsy of claim 21 further comprising positioning the second elongate body within the first elongate body.

23. The method of taking a biopsy of claim 21 further comprising removing a tissue sample from the second elongate body.

24. The biopsy instrument of claim 1, wherein the circumferentially extending slits each have a slit length, and wherein the slit lengths of the circumferentially extending slits are not uniform.

25. The biopsy instrument of claim 1, wherein said distal end comprises a beveled region of the elongate cannula body, and wherein the elongate cannula body further comprises a first portion between said distal end and said flexing region, and wherein said first portion is devoid of said slits.

26. The biopsy instrument of claim 5, wherein the uniform longitudinal spacing is between 0.012 inches and 0.03 inches.

27. The biopsy instrument of claim 14, wherein the uniform longitudinal spacing is between 0.012 inches and 0.03 inches.

* * * * *